United States Patent [19]

Lassen et al.

[11] Patent Number: 4,743,245
[45] Date of Patent: May 10, 1988

[54] LABIAL SANITARY PAD

[75] Inventors: Frederich O. Lassen, Winnebago County; Robert J. Peerenboom; Cheri L. Schultz, both of Outagamie County, all of Wis.

[73] Assignee: Kimberly-Clark Corporation, Neenah, Wis.

[21] Appl. No.: 891,701

[22] Filed: Jul. 30, 1986

Related U.S. Application Data

[60] Division of Ser. No. 707,338, Mar. 1, 1985, Pat. No. 4,631,062, which is a continuation-in-part of Ser. No. 654,927, Sep. 27, 1984, abandoned, and a continuation-in-part of Ser. No. 612,506, May 21, 1984, abandoned.

[51] Int. Cl.$^4$ .............................................. A61F 13/16
[52] U.S. Cl. ................................. 604/385 R; 604/378
[58] Field of Search .................... 604/385.1, 378, 379, 604/374, 375

[56] References Cited

U.S. PATENT DOCUMENTS

| | | | |
|---|---|---|---|
| 2,067,961 | 1/1937 | Williams | 604/385.1 |
| 2,092,346 | 9/1937 | Arone | 604/401 |
| 2,331,355 | 10/1943 | Strongson | 604/385 |
| 2,662,527 | 12/1953 | Jacks | 604/385 |
| 3,073,309 | 1/1963 | Mosier . | |
| 3,092,109 | 6/1963 | Mosier . | |
| 3,115,877 | 12/1963 | Harwood | 604/385.1 |
| 3,117,577 | 1/1964 | Mosier | 604/401 |
| 3,121,427 | 2/1964 | Mosier . | |
| 3,146,113 | 8/1964 | Mills . | |
| 3,183,909 | 6/1965 | Roehr | 604/385.1 |
| 3,406,689 | 10/1968 | Hicks et al. | 604/401 |
| 3,528,422 | 9/1970 | Hodas | 604/385.1 |
| 3,905,372 | 9/1975 | Denkinger | 604/385 R |
| 3,973,567 | 8/1976 | Srinivasan et al. | 604/385.1 |
| 3,983,873 | 10/1976 | Hirschman | 604/385 |
| 4,046,147 | 9/1977 | Berg | 604/385.1 |
| 4,079,739 | 3/1978 | Whitehead | 604/387 |
| 4,184,498 | 1/1980 | Franco | 604/387 |
| 4,321,924 | 3/1982 | Ahr . | |
| 4,340,058 | 7/1982 | Pierce et al. | 604/385 R |
| 4,360,022 | 11/1982 | Usami et al. | 604/378 |
| 4,372,312 | 2/1983 | Fendler . | |
| 4,397,644 | 8/1983 | Mathews et al. | 604/378 |
| 4,405,326 | 9/1983 | Lenaghan | 604/393 |
| 4,433,972 | 2/1984 | Malfitano | 604/385 |

FOREIGN PATENT DOCUMENTS

| | | |
|---|---|---|
| 2420339 | 8/1956 | France . |
| 754481 | 3/1978 | France . |
| 2513115 | 3/1983 | France ........................... 604/385.1 |
| 204076 | 4/1939 | Switzerland . |

Primary Examiner—John D. Yasko
Attorney, Agent, or Firm—Paul A. Leipold; Donald L. Traut; Jeremiah J. Duggan

[57] ABSTRACT

A labial pad (30) having an anatomically conformable configuration with a generally ovate geometry defined by a principal longitudinal axis (L), a minor transverse axis (T) and a generally orthogonal lateral or height axis (H), is comprised of a laterally upwardly directed projection (52) lying generally along the longitudinal axis within the posterior region (54) of the pad and having a prominence (64) proximate the distal end (60) thereof tapering toward the proximal end (58) along the longitudinal axis and to the opposed sides (62) along the transverse axis, wherein the projection is configured for disposition within the vestibule (32) of a wearer over a region bounded generally by the posterior labial commissure (36) and the labia terminating at or about the latter and extending forwardly therefrom over the vulva, to occlude the vestibule against flow of menses or the like while protecting the urogenitals from chafing contact.

2 Claims, 7 Drawing Sheets

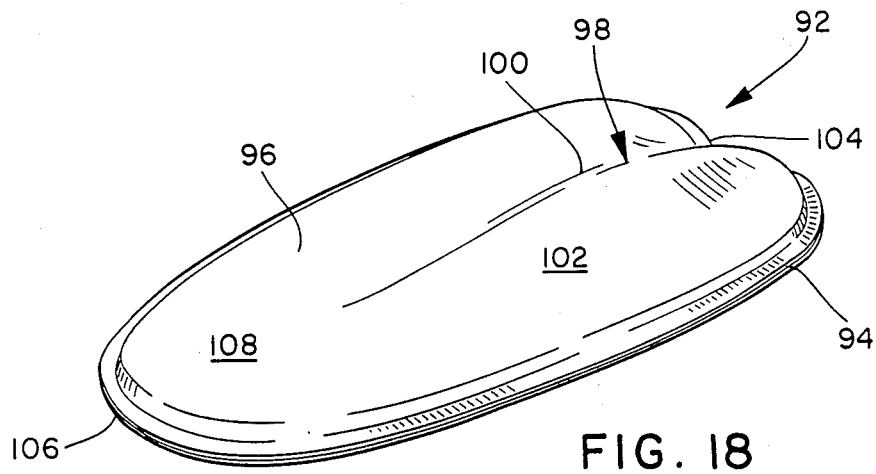
FIG. 18
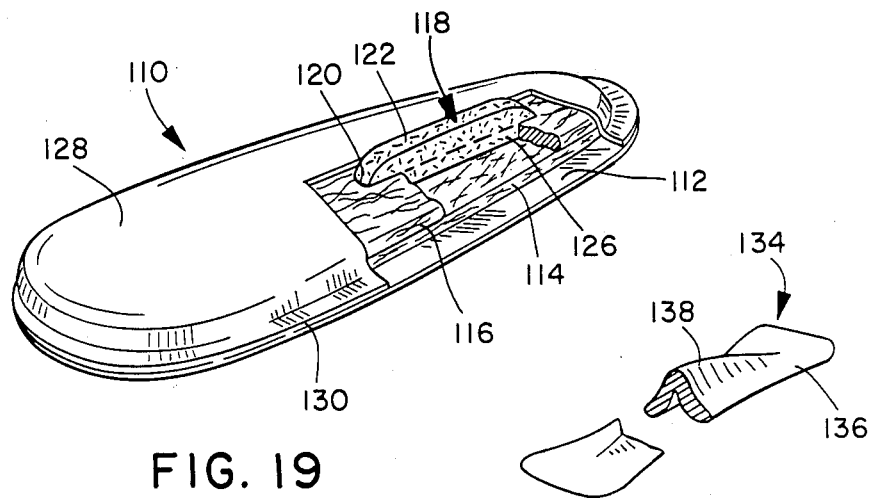
FIG. 19
FIG. 21
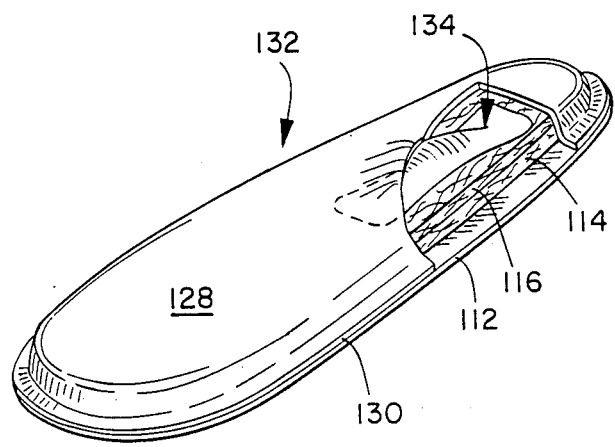
FIG. 20

LABIAL SANITARY PAD

CROSS REFERENCE TO RELATED APPLICATIONS

This is a divisional of co-pending application Ser. No. 707,338 filed on Mar. 1, 1985, now U.S. Pat. No. 4,631,062 which is a continuation-in-part of copending applications, Ser. No. 654,927 filed Sept. 27, 1984 abandoned Ser. No. 612,506 filed May 21, 1984 abandoned, identically entitled "Dynamically Shaped Pad," both of which are incorporated herein by reference and expressly relied upon.

TECHNICAL FIELD

The present invention relates, generally, to the field of sanitary napkins for personal feminine care or protection in order to absorb or otherwise contain menstrual fluids or similar exudate, perhaps urine as the consequence of minor incontinence, or the like. The present invention relates more especially to sanitary napkins shaped or contoured in order to achieve interposition within the vestibule of a wearer for occluding flow of body fluids prior to egress therefrom. Most particularly, the present invention concerns a labial pad offering enhanced fit and comfort through a novel construction which promotes a self-conforming anatomical cooperation of the pad with the wearer to yield a highly efficient catamenial device.

DESCRIPTION OF THE BACKGROUND ART

All manner and variety of devices or appliances configured for the absorption of such body fluids as menses are of course well known. As a class, these articles ought to possess certain necessary attributes of absorbency, comfort and psychological as well as physiological or physical protection. Desirably, these devices also are characterized as being discreet both during wear and when carried upon the wearer's person in anticipation of use. As will be seen from the ensuing discussion, these objectives are somewhat antagonistic in the sense that attainment of one has heretofore ordinarily necessitated comprising one or more other desirable feature.

The art has offered two basic types of feminine protection device with those objectives borne in mind; sanitary napkins or pads have been developed for external wear about the vulvar region of a user while tampons have been developed for residence within the vaginal cavity and interruption of menstrual flow therefrom. Each offers distinct advantages and, as one would expect, distinct or peculiar disadvantages, which range from psychological impediments and/or concerns to physical discomforture. Hybrid devices, attempting to merge the structural features of both within a single type of device, have also been proposed but have not seen a meaningful measure of acceptance insofar as the effort to appropriate advantages has been overshadowed by the more demonstrable perpetuation of structural and anatomically functional disadvantages. Inasmuch as the present invention relates to a labial pad, the foregoing types of feminine protection products are discussed below with that particular thought foremost.

Sanitary napkins, including contoured sanitary napkins such as those described in U.S. Pat. Nos. 4,397,644 and 4,079,739, are well known. Conceptualizing, sanitary napkins of this sort are of multilayered construction including a fluid absorbent core interposed within a backing of a fluid impermeable shield or baffle and a fluid permeable cover, the latter transmitting menstrual fluid or the like across its boundary to the absorbent core. As those skilled in the art will readily appreciate, the interrelationship of components is substantially more intricate; however, for purposes of basic understanding, the foregoing suffices. Within those very general parameters, one may also profitably compare the contoured sanitary napkin disclosed in U.S. Pat. No. 4,184,498. Given that conceptual background, there are several important requirements of such an article. Apart from the self-evident necessity that the core or absorbent member of a sanitary napkin must be constructed to retain menstrual fluid without leakage, there are two other features of conventional designs which warrant further attention in relationship to the present invention. These characteristics regard the cover member of the sanitary napkin and the manner in which the device is secured to or about the body of the wearer.

Dealing with the former first, the conventional wisdom respecting cover members for sanitary napkins dictates a composition or construction which yields a relatively dry and nonsmearing surface. There are both physical reasons and perceptual reasons to strive for those types of features. On the one hand, maximizing so-called "Z directional" flow, through the cover and into the absorbent or fluid retentive core, provides a means for accmmodating volumetrically greater discharges of menses during heavy flow conditions. On the other hand, this attribute minimizes the smearing effect and resultant discomfort experienced by the wearer. Psychologically, rapid Z directional flow with relatively dry cover conditions relates to the perception of safety which correlates with the potential for embarrassment upon failure of the napkin. Thus, for example, a major impetus for the improved comfort feature evidenced by, e.g., the invention disclosed and claimed in the aforementioned U.S. Pat. No. 4,397,644 is that type of dry cover with rapid transfer of menstrual fluid thereacross to the fluid retentive core member to achieve those specific goals.

Further along the general lines set forth above, positioning the sanitary napkin relative to the body of the wearer can be an important consideration. Over the last decade or so, sanitary napkins have now routinely been secured within or to the undergarment of a wearer. A move away from the historical tabbed napkin affixed about the body of a wearer by means of a belt or the like to adhesive attachment to undergarments is now almost universally complete in many significant commercial markets. This offers quite an advantage under most circumstances to a wearer as a matter of convenience. Nonetheless, a drawback persists in the nature of rubbing or chafing. More specifically, movement and particularly vigorous movement such as rapid walking or running yields motion between the body of the wearer (and particularly within the vulvar region) relative to an undergarment. Securing a sanitary napkin to the wearer's undergarment therefore translates under ordinary circumstances into relative motion between the wearer's body and the napkin itself, an experience exacerbated in fact as well as sensory perception should the cover fail to provide the features outlined generally above (e.g., a dry, nonsmearing cover). In turn, this can lead to heightened discomfort due to chafing, rubbing, and perhaps even to more intense irritation about highly sensitive tissues of the wearer. To date, these sources of discomfort have been begrudgingly accepted as a necessary concession where one wishes to utilize a sanitary napkin as opposed to a tampon for feminine protection.

Looking to tampons as such an alternative to sanitary napkins, the same are preferred by a substantial number of women. Offering the ability to intercept menses within the vaginal canal, the disadvantages inhering in sanitary napkins in respect of covers and attachment means are overcome by this approach. That is not to say, however, that tampons afford a superior means of feminine protection for all users. For example, there are many individuals who, for either physical or psychological reasons, are unable to utilize tampons as an effective means of feminine protection. Tampons themselves may be found lacking in terms of construction inasmuch as efficacy relies significantly on the ability of the same to undergo radial expansion upon fluid swelling in order to form a seal or zone of occlusion within the vaginal canal. Failure to do so implies overall failure of the tampon to serve as a reliable protection device.

As indicated briefly above, there have been proposals to merge the attributes of sanitary napkins and tampons into a single type of hybrid device. These hybridized appliances are generally classifiable by means of a prominence or projection designed for disposition within the vestibule of the wearer. In some instances, such as that suggested by the disclosure in U.S. Pat. No. 2,092,346, the pad includes a tampon component thereby physically adapting both approaches. That particular device and others of its ilk are typically found quite unacceptable for, amongst other reasons, the projection of a member through the vaginal orifice. Unlike a tampon which resides wholly within the vaginal canal, this type of device maintains constant interposition within the sphincter-like muscularture of the vaginal orifice which is decidedly disadvantageous from a comfort point of view. That discomfort can be substantially intensified where, in following the approach suggested by, e.g. the U.S. Pat. No. 2,092,346, the element within the vaginal opening is physically secured to an external member whereby relative movement of the wearer and the underlying pad structure compounds the irritating tendencies of the structure. Conceptually similar is the protective shield disclosed in U.S. Pat. No. 3,905,372. Although perhaps less prone to causing irritation within the sensitive tissues of the wearer, many of the same problems are found relative to the projection of an element through the vaginal orifice.

There have been several other approaches suggested in the art which purport or otherwise attempt to avoid the problems mentioned immediately above as regards the interruption of the vagina. For example, U.S. Pat. No. 3,983,873 suggests quite a wide array of geometries for a feminine hygienic pad configured for residence at least partially within the wearer's vestibule. The patentee places a premium on the use of relatively angular geometries for the structure, including, for example, a substantially abrupt change in transverse dimensions in order to yield shoulder-like configurations at the juncture between the anterior and posterior regions of the pad. Optionally, but preferably, the pad is formed with wings which are resiliently urged toward each other for bearing against the walls of the labial space in order to increase the retentive forces of the pad therein. Consequently, the design offered in the U.S. Pat. No. 3,983,873 is one which requires the sanitary pad to bear against the inner region of the wearer's vestibule which, in turn, is expected to be irritable and lead to discomfort over prolonged periods of use. Other so-called labial sanitary pads are disclosed in U.S. Pat. No. 2,662,527. The patentee in that case describes a pad composed of two portions. The first is deemed a main portion having a length sufficient to extend from a point between the wearer's frenulum and the rectum to a point opposite the anterior of the vestibule. The second portion is formed of one or more layers folded or rolled to yield an element having a somewhat greater height than width and secured or in some efficient manner disposed intermediate the length of the main portion. The second member, borne upon the face of the main member, is dimensioned to fit between the labia of the wearer, bearing against the vaginal orifice; thus, the second element is entirely in residence within the vestibule of the wearer reaching the floor thereof. Of somewhat related interest is the sanitary napkin disclosed in U.S. Pat. No. 3,406,689, insofar as that structure likewise includes an element or second member supported upon the top surface of a sanitary napkin, configured for overlapping disposition about the entire vulvar region and, from there, extending posteriorly of the vestibule of the wearer.

Labial pads of the foregoing varieties, designed with improved absorptive efficiencies as an apparently singular goal, have not properly accounted for the importance of anatomical cooperation with the wearer. Comfort is a lacking feature in use, in the sense that sensitive tissues are oftentimes distended by obtrusive geometries while structural elements of the pads find their way into rubbing contact with similarly highly sensitive urogenital members such as the wearer's vaginal orifice, urethral orifice and/or clitoris. Even short duration wear under such circumstances customarily results in physical reactions ranging from intense discomfort to mild pain. While the device of the U.S. Pat. No. 3,406,689 is perhaps of a design less irritable than, for example, many of the other contoured or profiled hybrid devices noted above, the extension of the napkin into proximate engagement with the wearer's buttocks contributes substantially to chafing or like abrasion, perhaps even physical movement of the napkin out of position due to rearward movement with the buttocks themselves during walking. Irrespective of such considerations, other vestibule-type sanitary napkins are disclosed in U.S. Pat. No. 2,331,355, U.S. Pat. No. 3,528,422, and U.S. Pat. No. 4,046,147, which are similar to those discussed above respecting anatomical functionality; none of which warrant further extended discussion herein but review of which may profitably be undertaken.

A noteworthy configuration for a sanitary napkin, vis-a-vis the structure of the present invention, is disclosed in U.S. Pat. No. 3,073,309, although the same would not likely be classified as a labial pad per se by the skilled artisan. Related closely to that configuration are the generally similar constructions found in U.S. Pat. No. 3,117,577, U.S. Pat. No. 3,092,109, and U.S. Pat. No. 3,121,427. As common factors, these patents disclose a sanitary napkin having means for attaching the same about the body of a wearer and further including a raised element at the distal end of the pad, tapering in both forward and side directions. In the U.S. Pat. No. 3,073,309 this projection is denoted as an "indicating device," included in order to give the wearer assurance that the napkin is properly placed. To achieve that indicating function, the projection is said to be formed in such a way that it seats itself between the wearer's frenulum and rectum projecting upwardly into that region (i.e., the perineum) from the pad. Although expressly distinguished from a labial pad (normally thought to extend into the vestibule) and also a conventional tampon, the patentee there observes that this projection into the perineum will provide an effective damming action deterring rearward seepage of menses when the wearer is in a lying or supine position. An interesting point is articulated by the patentee in this connection; conventional devices which extend into the vestibule area between the labia contribute to irritation not encountered when the sanitary napkin of that (i.e., U.S. Pat. No. 3,073,309 reference is utilized, while the "damming" action is nonetheless allegedly attained by virtue of the design of the subject patent.

Devices heretofore proposed for partial or complete interposition within the vestibule of a wearer have uniformly failed to achieve any real measure of success for several reasons. For example, many have been designed simply with ancillary projections or the like for disposition within the vestibule but without overall regard for anatomical vagaries among wearers. In turn, placing a prominence or other projection entirely within the vestibule promotes the kind of irritation noted by the patentee in the U.S. Pat. No. 3,073,309 reference cited above. Furthermore, certain of the aforementioned designs have been made with an eye toward forcing the vestibule as a conformable tissue to mold about the generally more rigid projection or prominence, not unlike the interrelationship between vestibule and pad required in the U.S. Pat. No. 3,983,873 where the article includes shoulder-like configurations and wing elements as important structural features to ensure anatomical cooperation. Irritation or tendencies toward that effect is most often a consequence where no accommodation is made for the fact that the body of the wearer can have substantial relative movement respecting the pad depending upon the manner in which the latter is associated with the former. As noted above, firmly securing a pad to the undergarment of a wearer with a portion of the pad located within the vestibule will under most circumstances be found to create a rubbing or chafing effect within that very sensitive environment. The attempts summarized above have also failed to take into account the specific nature of that sensitive environment, one which is typically a moist, highly sensitive tissue (said to approach a mucous membrane) in contradistinction to "external" skin. Consequently, adaptation which simply converts a normal sanitary napkin having a cover which is designed, perhaps specifically, to exhibit an advantage of being dry and disposing that within the more moist or hydrous environment of the vestibule can lead to substantial discomfort.

Accordingly, those skilled in the art will readily appreciate that there has yet to be devised a labial pad which achieves the goals set forth throughout the prior art discussed above relative to contoured sanitary napkins but which will overcome the serious disadvantages heretofore proving to be serious impediments to their acceptance, whether viewed technically or commercially. The present invention fulfills that long felt need.

DESCRIPTION OF THE INVENTION

It has now been determined in accordance with the present invention that a labial pad can be provided which approaches the occluding advantages offered by a tampon, in the sense that menses or the like may be interrupted prior to egress from the vestibule, while the safety of a sanitary napkin or pad is maintained. Advantageously, the labial pad of the present invention, and specifically the absorptive core thereof, achieves considerably improved fluid distribution and retention thereby allowing savings in size. The design of the labial pad of the present invention is such that it requires only partial insertion within the vestibule to be successful, avoiding proximate contact with the more sensitive, urogenital portions of the anatomy. Further advantageous, as a particular consequence of a novel configuration, the labial pad of the present invention is anatomically self-conforming thereby providing a positive zone of occlusion without distention of the sensitive tissue comprising the vestibule or its surrounding regions. That contributes, in turn, to the further and significant advantage that the pad of the present invention does not require external attachment either to the wearer's anatomy or undergarments proximate the same, minimizing significantly the irritability factor heretofore characteristic of similar devices.

The foregoing, and other advantages of the present invention, are realized in an anatomically, generally self-conforming sanitary napkin or pad configured for partial labial disposition within the vestibule of a wearer for at least partially occluding the same respecting fluid flow therefrom. The labial pad of the present invention in one aspect thereof is comprised of a fluid absorbent body having a posterior region including a raised profile for projection within the vestibule intermediate the labia majora inwardly bounding the same from a position posteriorly remote from the clitoris and extending to the rearwardmost aspect of the vestibule, preferably terminating at or about the location of the frenulum. An anterior region of the pad merges with the posterior region for a generally external disposition about the vulvar region of the wearer over the labia majora and spaced from the clitoris thereby protecting the same while simultaneously avoiding rubbing or chafing contact with that sensitive anatomy. The pad of the present invention is most preferably comprised of a fluid absorbent body having a top, body-side surface, a bottom, garmentcontacting surface, and perimetral sides defining an overall geometry, wherein the raised profile is developed within the top surface of the posterior region. Most preferably, the fluid absorbent body includes a generally longitudinal pleat extending from the posterior region centrally along a longitudinal axis for establishing a raised profile precursor having a generally transverse curvature with regard to the pleat. Adhesive elements (or functionally equivalent thermal bonds) may be included within the interior apex region of that longitudinal pleat at the bottom side surface of the pad in order to maintain the proper profile for the labial projection. Incorporating several such (adhesive) junctures which are selectively interruptible allows the wearer to make specific adjustments to the profile in order to account for anatomical vagaries as need be.

The raised profile or precursor is disposed within the vestibule in contact with the surrounding tissue to form a line of occlusion preventing egress of menses or similar body fluids, while the forwardmost portion or anterior region of the pad folds beyond the vestibule about the vulva of the wearer. The self-conformity of the pad, allowing it to mold in an individual manner to accommodate the specific body structure of the wearer, is sufficient to preclude the necessity for external attachment members or elements to maintain the pad in proper position. Hence, the pad moves with the wearer regardless of movement of undergarments or the like; albeit, the slight external pressure of the wearer's undergarment is generally required to provide a type of biasing of the pad into its proper position. Optionally, but entirely unnecessary under most circumstances, the pad of the present invention includes a restricted or limited spot or zone of attachment adhesive or the like; a single, discrete adhesive element which, if used at all by the wearer, is positioned as close as is possible to the neutral zone of the undergarment to minimize tendencies toward relative motion between the undergarment and the pad itself.

In another aspect of the instant invention, the fluid absorbent body is preferably comprised of a microfibrous web. Although the web may be selected from any one of a number of hydrophilic or suitably treated hydrophobic fibrous materials, most preferably the pad of the present invention includes a web of polypropylene microfibers (or equivalent polymeric microfibers) bearing or otherwise suitably incorporating a surfactant. Still further along these lines, it is preferred that the absorbent body be comprised of a plurality of individual layers of microfibrous webs laid in generally face-to-face engagement in a lateral direction. Also preferred is an arrangement wherein the microfibrous webs are disposed generally edgewise immediately along the longitudinal axis of the pad within the posterior region and generally facewise across the transverse axis within the anterior region and along the perimetral edges in the posterior region. This provides the most favored orientation for rapid Z directional wicking of fluid within the region of occlusion while optimizing both internal distribution of fluid and the ability of the pad to accommodate excess fluid during times of heavy flow; while increasing the adaptability of the pad to variations in individual anatomy, user to user.

Improved comfort is achieved by incorporating a physiologically hydrous cover over the absorbent body of the pad of the present invention. In concert with a transfer layer intermediate that cover and the most preferred microfibrous batts, Z directional flow of fluid is optimized while a physiologically acceptable interface is ensured. Along these lines, it is envisioned that the "hydrous" feature for the cover may be provided either across the entirety of the pad structure or, should it be desired, may be achieved by such expedients as coatings within at least that region in proximate engagement with the hydrous or moist environment of the tissue of the wearer's vestibule in order to optimize compatibility.

Other advantages of the present invention in terms of both construction and mode of operation, as well as a fuller appreciation for its manufacture and use, will be gained from an examination of the following detailed description of preferred embodiments, taken in conjunction with the figures of drawing.

BRIEF DESCRIPTION OF THE DRAWINGS

FIG. 18 is an isometric view of an alternate embodiment of a labial pad in accordance with the present invention;

FIG. 19 is an isometric view, with parts broken away, illustrating still a further alternate embodiment of a labial pad in accordance with the present invention;

FIG. 20 is an isometric view, again with parts broken away, illustrating yet another alternate embodiment of a labial pad in accordance with the present invention, in this case including a moveable insert within the posterior region of a pad; and, FIG. 21 is a fragmentary isometric view of the insert employed within the alternate embodiment illustrated in FIG. 20.

DETAILED DESCRIPTION OF THE PREFERRED EMBODIMENTS

The present invention relates, generally, to sanitary napkins for personal feminine care or protection in order to absorb or otherwise contain menstrual fluid or similar exudate, perhaps urine as a consequence of minor incontinence, or the like. The present invention relates more especially to sanitary napkins shaped or contoured in order to achieve interposition within the vestibule of a wearer for occluding flow of body fluids prior to egress. Most particularly, the present invention concerns labial sanitary pads offering enhanced fit and comfort through a novel construction which promotes a self-conforming anatomical cooperation of the pad with the wearer to yield a highly efficient catamenial device. Accordingly, the present invention will now be described with reference to certain preferred embodiments within the aforementioned contexts; albeit, those skilled in the art will realize that such a description is meant to be exemplary only and should not be deemed limitative respecting the scope of the present invention, for example in terms of its construction and mode of operation.

Figure 1:
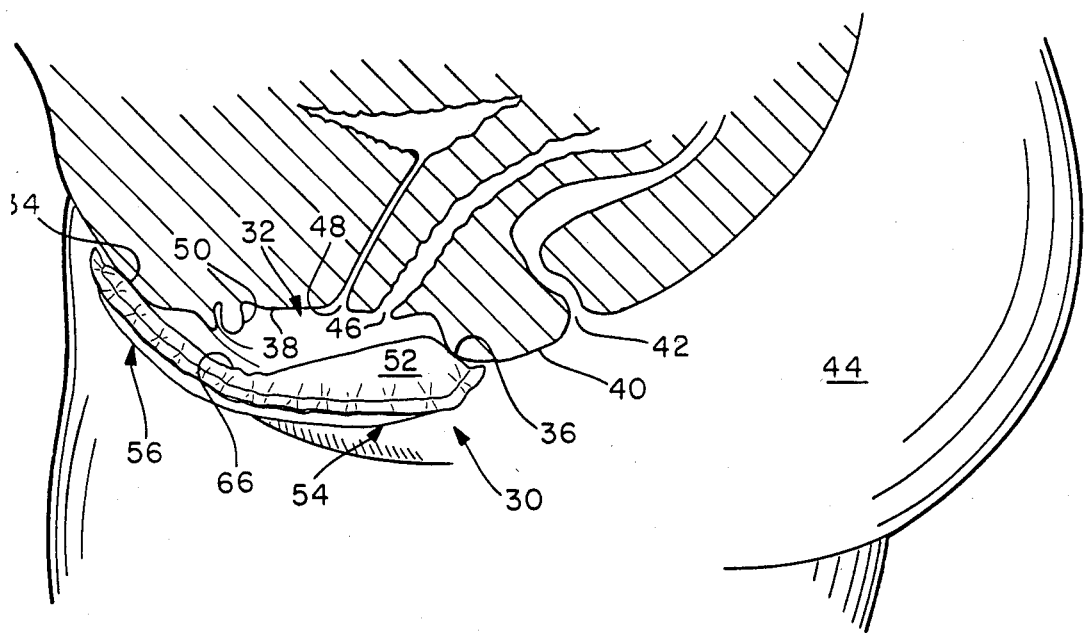
FIG. 1 is a simplified anatomical section illustrating the environment for a labial pad in accordance with the present invention, shown in residence within the vestibule of a wearer.
Figure 2:
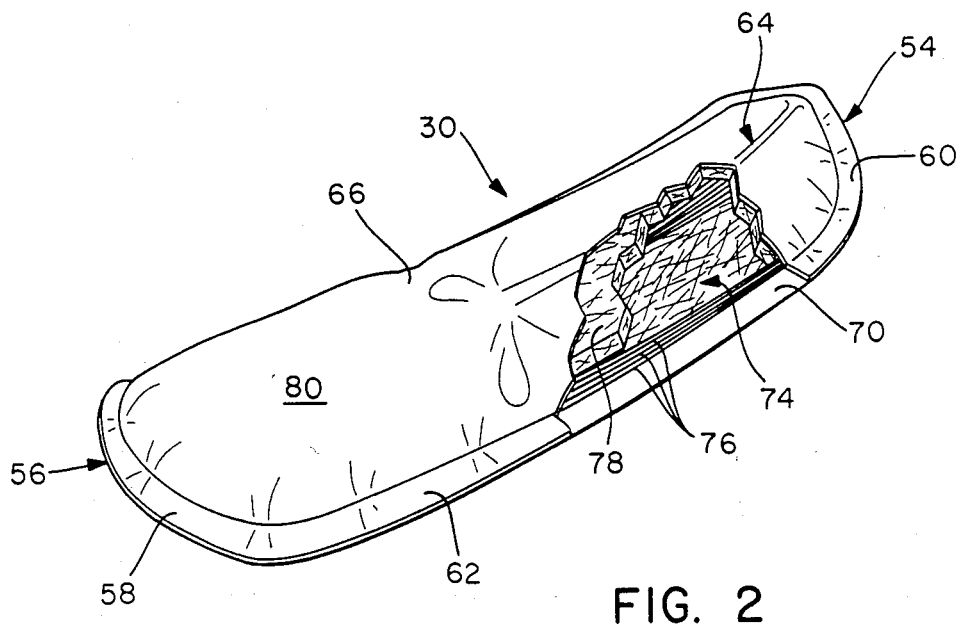
FIG. 2 is an isometric view of a labial pad in accordance with the present invention, with parts broken away to reveal internal components thereof.

Turning to the figures of drawing, in each of which like parts are identified with like reference characters, FIG. 1 illustrates diagrammatically a labial pad in accordance with the present invention designated generally as 30, disposed within the vestibule of a wearer, designated generally as 32. As used herein, the term "labial pad" connotes a sanitary napkin or like article of commerce having a portion specifically configured for disposition between the labia majora, extending into the vestibule, or particularly adapted to achieve that anatomical conformity when put to use. For purposes of the ensuing description, the vestibule is considered to be the region defined within the labia (not specifically shown in the figures herein) beginning at about a point lying caudally from the anterior labial commissure 34, extending rearward to the posterior labial commissure 36 and bounded inwardly by the floor 38. Those skilled in the art fully understand that there is a wide range of variation among women with respect to the relative size and shape of labia majora and labia minora as the same interrelatedly define the contours of the vestibule. For purposes of the present description, however, such differences will not specifically be addressed, it being recognized that in any event the disposition of the labial pad of the present invention into the vestibule will necessitate placement between the labia majora regardless of any such consideration respecting the labia minora. Lying caudally of the vestibule 32 is the perineum 40 which leads to the anus 42 in the region of the buttocks 44. Within the vestibule itself is located the principal urogenital members which, for purposes pertinent here, are constituted of the vaginal orifice 46, the urethral orifice 48, and the clitoris 50. Given the foregoing simplified review of this anotomical region, and to facilitate the present description, the vestibule will be considered generally to be the region between the clitoris 50 and posterior labial commissure 36, for convenience sake. For a fuller description of this portion of the female anatomy, however, attention is invited to Gray's Anatomy, Clemente 30th Ed. (1985) at 1571-1581.

As can be seen with reference to the anatomical structure depicted in FIG. 1, the labial pad 30 of the present invention is disposed partially within the vestibule 32 for occluding the same respecting fluid flow therefrom. In this regard, the predominant use of the labial pad 30 is for the absorption of menstrual fluid emitted via the vaginal orifice 46; although the labial pad of the present invention is equally well adapted to serve as a type of incontinence device for absorption of urine as occurs upon minor, female incontinence. Without particular regard to the type of fluid to be intercepted, the labial pad 30 includes a raised projection or profile identified generally as 52 lying within the posterior region of the pad, denoted generally as 54. The raised profile 52 is that region of the pad which protrudes within the vestibule and does so intermediate the labia majora inwardly bounding same from a position beginning posteriorly remote (and slightly caudally) from the clitoris 50 and extending to the rearwardmost aspect of the vestibule 32, abutting the posterior labial commissure 36 and generally occluding that region of the vestibule against, e.g., menses. As best viewed in FIG. 1, the projection within the posterior region the pad is most preferably dimensioned or otherwise contoured to avoid contact with the urogenital elements of the wearer's anatomy. In the context of this description, the term "projection" is employed to convey the thought that the pad 30 includes a component, preferably integral therewith or otherwise a part thereof, which "projects" upwardly from the external interface or plane of the pad and the wearer's vulva to reside at least partially within the vestibule (i.e., upwardly from a location between the labia). The "projection" may be entirely coincident with the "profile," although that is not a structural requirement nor are the two terms employed herein necessarily synonymous for purposes of interpretation. Continuing further with this concept, the projection can be visualized to include a "prominence," which connotes the region of the projection which rises to the highest point as measured from the above-mentioned interface or plane. With the foregoing definitional background, the skilled artisan will understand that these terms do not necessarily compel the presence of a free standing structure which is shape sustaining prior to use, in the sense that a clearly defined projection is structurally identifiable prior to disposition within the vestibule to occlude the same. Quite to the contrary, the projection may be fairly ill-defined or unrecognizable prior to use of the pad 30; however, upon proper anatomical cooperation between the pad and the vestibule of the user as occurs upon use, the structural forms or features will taken on the definitive shapes shown and described herein. For example, in certain embodiments of the present invention, the labial pad may have an overall shape prior to use visually indistinguishable from a conventional "mini pad," yet when put to use it will adopt the profile described above. Accordingly, those skilled in the art will appreciate that the figures herein and description thereof represent but one visualization of these elements of the invention for the convenience of a complete portrayal.

The pad 30 also includes an anterior region identified generally as 56 which merges with the posterior region 54 generally intermediate the overall length of the pad. The anterior region 56 is configured for external disposition about the forward vulvar region toward the mons pubis, over the labia majora and spaced from the clitoris 50 such that the highly sensitive genital tissue is not in contact with the pad but is, to the distinct contrary, spaced or isolated therefrom. In this manner a line of occlusion is defined in a very general sense within the raised profile of the posterior region of the pad where the same merges into contact within the vestibule of the wearer over the region bounded generally by the posterior labial commissure and the labia majora merging to a point spaced from the clitoris as aforesaid. A general representation of that occluding line within which lies a target zone for receipt of menses or like exudate is depicted generally as the teardrop shaped region best viewed in FIG. 4, the intention there being simply to idealize the representation of that zone. Those skilled in the art will appreciate that the vast anatomical differences to be encountered among the population of users for these types of devices imply widely varying contours for that target zone or line of occlusion; the ability of the instant pad to achieve a self-conforming anatomical cooperation with that wide array of potential anatomical variations being a significant advancement in this art as will be realized further as this description continues.

Figure 3:
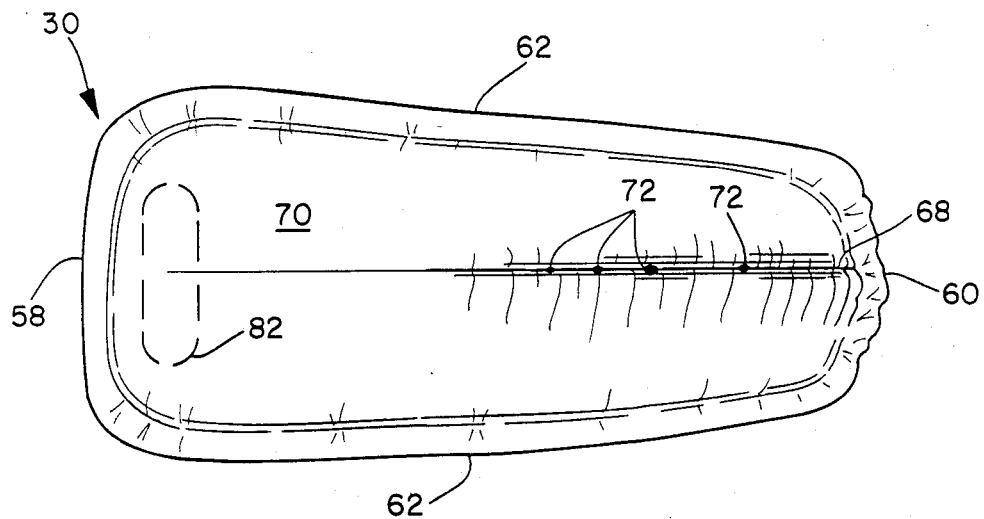
FIG. 3 is bottom plan view of the labial pad shown in FIG. 2 illustrating, in phantom, an optional adhesive element for securing the pad to the undergarment of the wearer.
Figure 4:
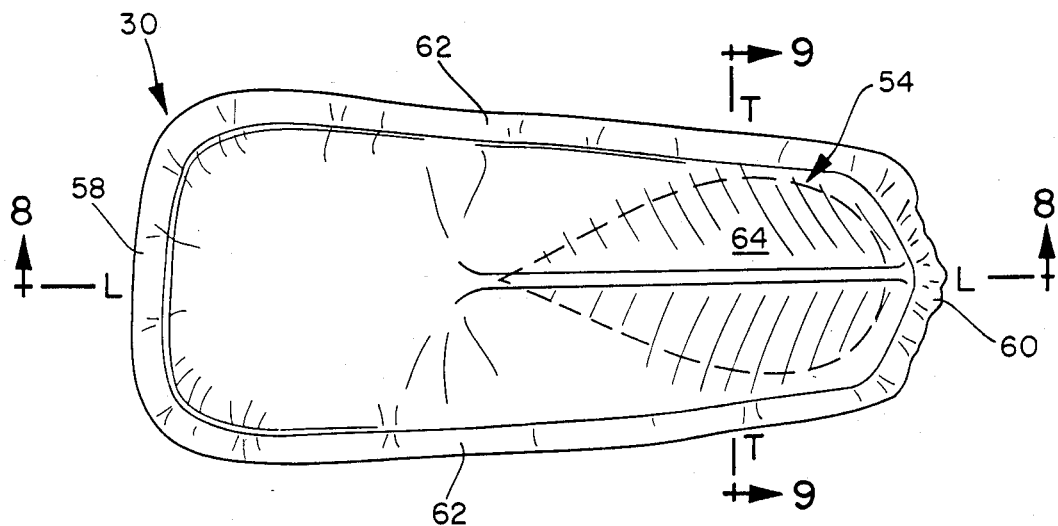
FIG. 4 is a top plan view of the labial pad of the present invention, illustrating in phantom a "target zone" or that portion of the pad destined for interposition within the wearer's vestibule and receipt of fluid.
Figure 5:
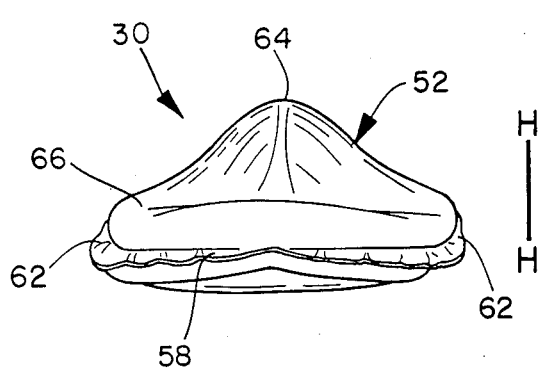
FIG. 5 is an end elevation view from the proximal end of the pad at the present invention.

The pad 30 is shown in its most preferred embodiment to have a generally ovate geometry extending between a proximal end 58 and a distal end 60; e.g., as exemplified in FIGS. 3 and 4, to be slightly wider at the former than the latter. This preferred ovate geometry, including the raised profile of the posterior region 54, is conveniently related to three axes identified in FIGS. 4 and 5 as a principal longitudinal axis "L," a minor transverse axis "T" and a lateral (or height) axis "H." Thus, to complete the overall geometric orientation for purposes of this description, the pad 30 includes longitudinal sides or edges 62 ranging between the ends 58 and 60, these collectively sometimes being referred to herein as the perimetral sides or edges of the pad 30 (i.e., those defining the perimeter). Considering briefly the relative dimensions of a preferred pad, in a functional sense, the same is at least long enough along the longitudinal axis to extend (in use) from the frenulum forward (without significant overlayp thereat) to and over the anterior of the vulva; its width as considered across the transverse axis being limited to avoid contact with the legs of the wearer when in use.

Figure 6:
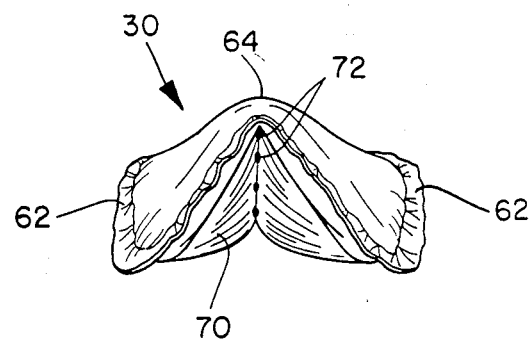
FIG. 6 is an end elevation view from the distal end of the pad of the present invention.
Figure 7:
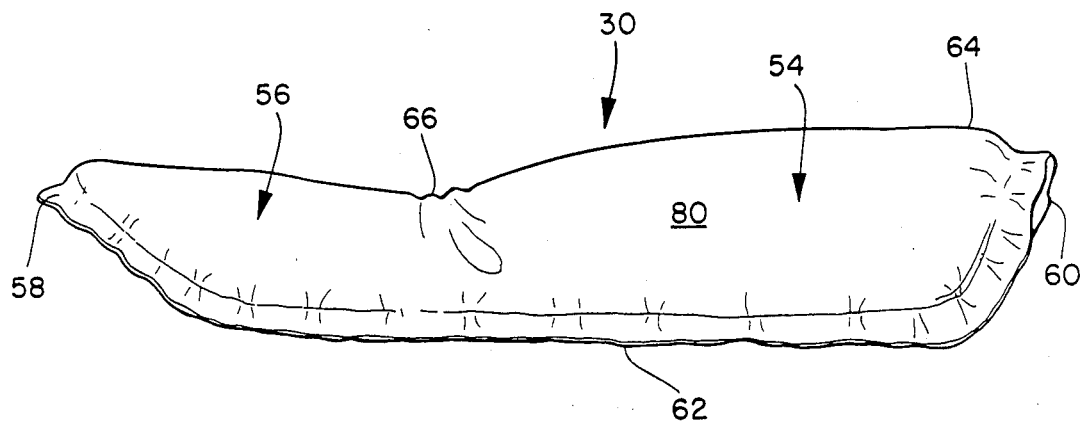
FIG. 7 is a side elevation view of the pad of the present invention.

The raised profile 52 of the pad 30 preferably lies entirely within the posterior region 54 thereof. From a prominence 64 proximate the distal end 60, the profile tapers gently toward the proximal end 58 in the longitudinal direction and also toward the opposed longitudinal sides 62 in the transverse direction, as best viewed, for example, in FIGS. 5-7. The profile continues with a taper or downward slope in the forward direction to a juncture 66 with the anterior region which, in the embodiment illustrated, has a very gradual rise toward the proximal end 58 but of lesser slope than that in the posterior region. Inasmuch as the composition of the pad 30 is, overall, relatively compressible with slight resilience, and further insofar as the pad is intended to be generally self-conforming in use, those skilled in the art will appreciate that this structure is flexible and may be imparted with other similar suitable shapes without necessarily departing from the spirit of the present invention. Because of this ability of conformance and ease of flexibility, the raised profile is most preferably impressed in the overall structure by means of a profile precursor established within the pad itself. This may be achieved in one preferred aspect of the invention by providing a longitudinal set to the pad; i.e., a preferential fold or crease along the longitudinal axis as best viewed in FIGS. 3-6, which tends to pitch the pad upwardly along that fold. In this case, a longitudinal pleat 68 is formed within the bottom face or surface 70 of the pad, which, in turn, creates the prominence 64 contributing to the raised profile 52; whether as a strict manufacturing consequence and, hence, as a shape-sustaining structural element prior to use or, alternatively as a zone or line of structural partiality which creates the profile due to conformance in use. In the highly preferred form shown in these figures, the bottom surface 70 is comprised of the conventional baffle member or fluid impervious shield customarily incorporated within a sanitary napkin. Advantageously, therefore, as a polymeric film or nonwoven material bearing a polymeric film, the set or pleat developed upon folding will yield a highly preferential crease line along the longitudinal axis "L." Several options have been devised to complement this longitudinal folding of the pad, or even supplant it, with the objective of establishing a preferential development of a profile precursor. For example, the absorbent body may be slitted along or proximate the longitudinal centerline or axis. The slit may be completely through the absorbent core relative to the "H" axis. Likewise, the slit may be continuous along the core relative to the "L" axis, or discontinuous; i.e., in respect of the latter option, a perforated line contributing to the preferential fold or set. Depending upon the nature and composition of the core, as explained more fully below, the set may be established by an embossment. Other approaches will occur to the skilled artisan for achieving the goal of, ultimately, providing the profile precursor which, in turn, assists in the most advantageous anatomical cooperation between the pad and the wearer.

It is preferred to maintain this profile precursor achieved through the pleat 68, or through whatever other option is elected, in a relatively permanent configuration. The orientation may be conveniently ensured as a somewhat enduring one by means of at least one and preferably several adhesive junctures 72 disposed within the interior apex of the pleat as best viewed, for example, in FIG. 3. Under most circumstances, a single juncture 72 spaced suitably from the distal end 60 will suffice to maintain the profile precursor in an adequate shape to accommodate the anatomical variations to be anticipated amongst most users. Optionally, however, an added measure of adjustability can be included by providing a series of adhesive junctures or bond points such as shown in the figures of drawing, wherein each bond point is selectively interruptible. In that manner, the user may tailor the length and prominence dimensions of the projectioon 52 by suitably interrupting (i.e., breaking) one or more of those adhesives junctures 72 prior to use. Thus, the range of sizes and geometries achievable by means of the present invention are both extended significantly. Other similar variations are envisioned for providing additional user conveniences in tailoring specific dimensional variations to suit individual preferences. A single line of such selectively interruptible bond points as shown in the figures allows the user to adjust the location of the prominence 64, particularly relative to the longitudinal axis "L." Staggering those gond points in a "W"-like zig-zag pattern permits further adjustability in the height of that prominence. As the skilled artisan will appreciate, these junctures or bond points 72 need not be adhesively formed, but may result from thermal bonding or the like, particularly in those situations where the bottom surface of the pad is composed of a polymeric baffle member. Likewise, a zone of adhesive may optionally replace the discrete junctures should that be a desirable approach. Regardless of the mode of implementation, through, the objective of selectively tailoring the pad dimensions is advantageously provided as a user option.

Figure 8:
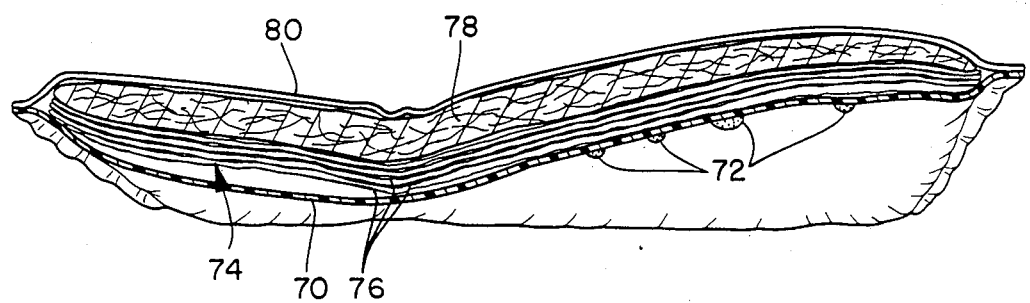
FIG. 8 is a longitudinal sectional view, taken substantially along the line 8—8 of FIG. 4.
Figure 9:
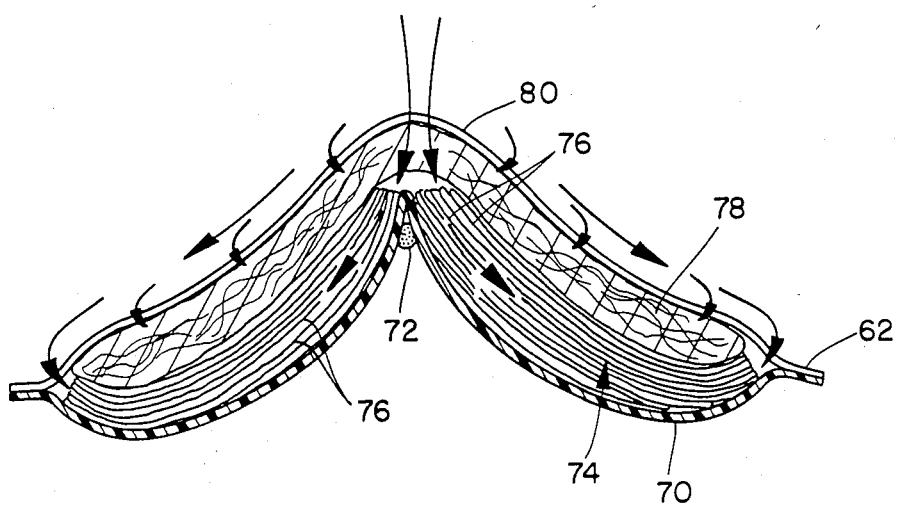
FIG. 9 is a transverse sectional view within the posterior region of the labial pad of the present invention, taken substantially along the line 9—9 of FIG. 4, and further illustrating the flow pattern (both principal and secondary) of body fluids received by the instant pad and distributed thereabout.
Figure 10:
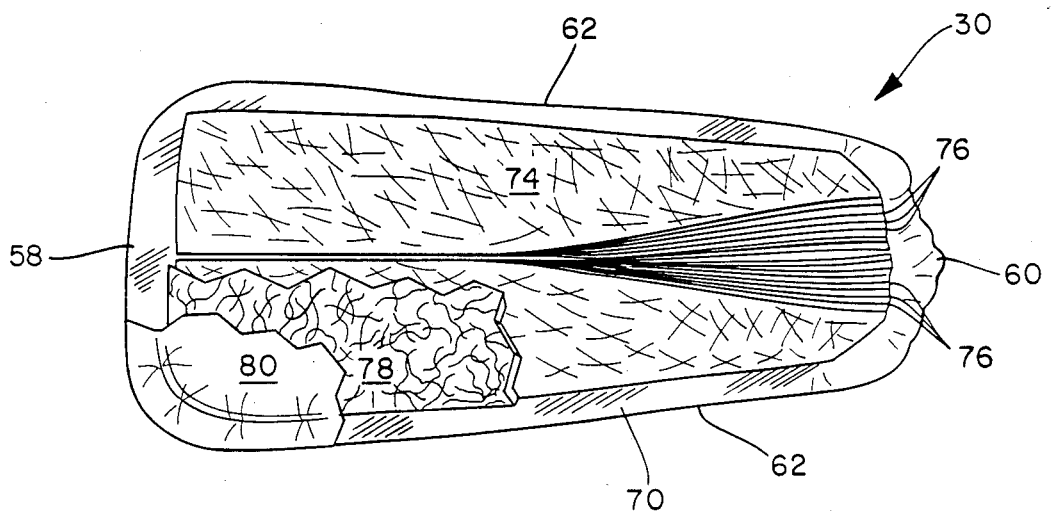
FIG. 10 is a top plan view of a pad in accordance with the present invention, similar to that of FIG. 4, but with parts broken away to illustrate the preferred orientation of microfibrous webs within the absorbent body thereof.

The absorbent capacity of the pad 30 of the present invention is provided by a fluid retentive core or absorbent body identified generally as 74. In general, the absorbent body 74 may be comprised of any conventional absorbent composition including, for example, cellulosic batt(s). However, the highly preferred structure for the absorbent body 74 illustrated in the figures of drawing is in the nature of a microfibrous absorbent. More preferable yet, the absorbent body 74 is comprised of a plurality of individual microfibrous webs 76 disposed in generally face-to-face engagement within longitudinal zones lying along the longitudinal centerline "L" of the pad 30. Most preferably the microfibrous batts 76 are located in a highly efficient orientation, with the batts being placed edgewise within the posterior region immediately across the longitudinal axis (and thus within the target zone) while lying facewise in the anterior region and along the perimetral edges of the posterior region. This relationship is best viewed with reference to FIGS. 8-10, showing the manner in which the composite of microfibrous batts twists along the longitudinal axis to achieve that highly preferred orientation. This presents the most effective angle of incidence for capillarity within the target zone to achieve rapid wicking distribution of menses or the like with correlative fluid distribution in the X-Y direction once received within the absorbent core, a feature considered in greater detail below. The microfibrous webs may be replaced by other wicking or absorbent materials adapted for retention of fluid, and preferably a batt or member having absorbent characteristics approaching the capillarity of microfibers. A suitable alternative in many cases is a densified cellulosic fiber web with a density in the range of from about 0.15 to about 0.30 gm/cc. and preferably about 0.2 gm/cc. Regardless of the absorbent core adopted, whether one of the foregoing or an equivalent, a transfer layer 78 overlies the core to assist in this preferred fluid distribution, as also noted below.

Figure 17:
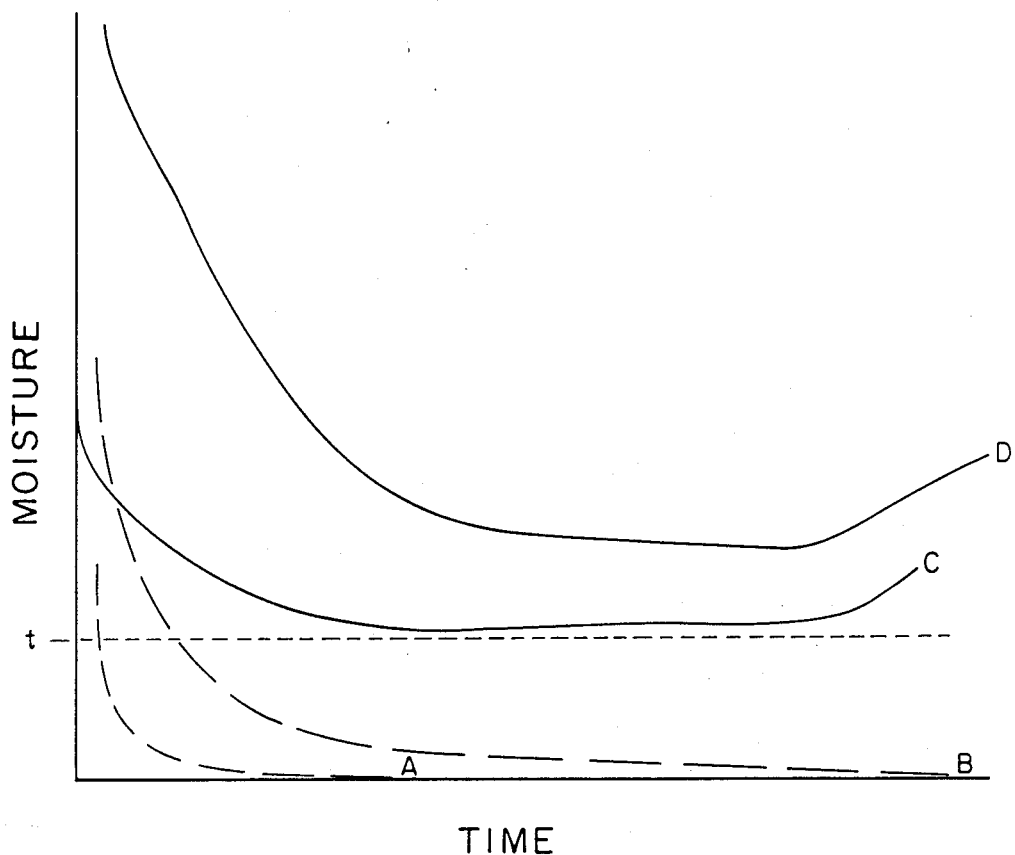
FIG. 17 is a simplified graph showing a comparison of the moisture characteristics of various cover materials for a labial pad of the present invention as contrasted with conventional cover materials for a sanitary napkin.

Completing the overall structure of the pad 30 is a cover member 80 which optimally possesses certain characteristics particularly selected on account of the labial disposition of the pad relative to the wearer. The conventional wisdom respecting cover materials for sanitary napkins has been pointed toward materials and/or structural orientations which yield two specifically desirable attributes. On the one hand, rapid Z directional transmission of fluid through the cover and away from the wearer's body has been of paramount concern to those working in this art over the years. Second, and closely related, is the desire to provide a dry cover for that interfacial member which is in proximate engagement with the wearer's body. For both physical and psychological reasons, it has been quite important for conventional sanitary napkins to have a dry, nonsmearing interface achieved by optimizing those two characteristics. However, that approach is deemed generally antithetical to the labial pad of the present invention, inasmuch as the same must function within the more hydrous and sensitive tissues of the wearer's vestibule. More specifically, the labia majora and labia minora which bound the gross anatomy of the vestibule include delicate tissues and membranes which are physiologically hydrous in the sense that the same maintain an ideal level of moisture within the urogenital region. Disposing a conventional cover material within that environment, designed to wick rapidly in a Z direction, would contribute to a drying of that sensitive tissue. That would be a most unwelcomed result inasmuch as chafing or other irritability of these delicate tissues would be quite uncomfortable for the wearer. However, it has been determined in accordance with the present invention that the use of a physiologically hydrous cover 80 overcomes those impediments and yields a highly advantageous pad construction. As used herein, that term "physiologically hydrous" is meant to connote a cover material which maintains a suitably moist interface between the tissues of the vestibule and the pad 30 when disposed in that vestibular environment; one that is benign respecting the requirements of comfort associated with the interposition of fabric or fabric-like structures within the moist tissue environment of the vestibule, keeping in mind as well the self-evident factor that the pad is receiving body fluids migrating through the vestibule and must conduct the same to the absorbent core. Thus, while not "hydrous" in the classic sense prior to use (inasmuch as the cover will be dry at that time) the cover maintains (or at least does not interfere with the maintenance of) the proper moisture level or balance required within the vestibule. For example, in considering this feature of physiologically hydrous covers, and with specific reference to FIG. 17, there is shown the response of four different types of cover materials identified A-D correlated with comparable transfer layers. The graph represents the moisture level responses for each of the four materials sampled relative to the time for wicking during normal menstrual flow. Further included is a horizontal indication of a threshold moisture level identified "t," above which optimal results obtain. The curves which are represented in FIG. 17 are generated very simply upon time measurement of the fluid level characteristics of the cover member of a sanitary napkin when associated with the remaining components constituting that structure. That is, for purposes of establishing a quantitative measure to isolate nonacceptable cover candidates from those which meet the requirements of a physiologically hydrous cover in accordance with the present invention, the test is conducted on a cover member when structurally associated as a component of a sanitary napkin. Either a finished sanitary napkin may be used or one constructed simply for testing since a particular cover may be susceptible to wicking variation as a function of the wicking characteristics of an associated transfer layer and the rewetting characteristics of a fluid retentive core. In an effort to establish such a quantitive measure with an eye toward discriminating between acceptable and nonacceptable covers, the fllowing test has been adopted.

A sanitary napkin bearing a cover to be screened is wetted with a measured quantity of water. For purposes of the present test, a discrete spot of ten milliliters of water is deposited centrally of the pad to be examined. That moistened pad is placed on a partially filled resilient water bottle (e.g., a conventional household hot water bottle) which is supported upon the top plate of a laboratory jack. Disposed above the jack is a stationary plate against which the pad, borne upon the water bottle, may be urged. Prior to that, however, a moisture probe is located intermediate the wetted portion of the test specimen and the stationary plate. The test is conducted utilizing a commercially available moisture probe marketed by the "Greenthumb Products Company" of Apopka, Fla., U.S.A., intended by the manufacturer to be a houseplant moisture tester. Since the test adopted here is of the "go," "no-go" variety, any probe or other like instrument capable of developing a signal in response to the presence of moisture is equally well adaptable for a similar test, particularly inasmuch as the data of interest are advantageously normalized to the condition of the vestibule, eliminating the need for strict quantitative measurement. The test apparatus couples the probe to a meter with a graduated scale, the precise graduations being of less interest here since relative time/moisture measurements are of concern. With the probe in place, the laboratory jack is raised to establish a pressure of 0.5 psi, conveniently measured through the displacement of water from the resilient water bottle supporting the test specimen. A timer is started when that pressure reading is attained and the gauge readings are recorded at 30 seconds, 60 seconds, 120 seconds, 240 seconds, 300 seconds, 600 seconds and 900 seconds. Those readings are plotted on a relative moisture scale as represented in FIG. 17 against the benchmark or threshold level "t" representing the moisture level below which a statistically significant sample of users would find the cover material to be objectionable due to an inability to maintain the necessary physiologically hydrous interface between the prominence of the pad and the vestibule within which it is located during use. Other tests may be adapted to this same end, the foregoing being deemed representative of the preferred approach to be taken in order to characterize suitable materials with these thoughts in mind.

The covers identified as A and B in FIG. 17 are based upon the materials disclosed and claimed in U.S. Pat. No. 4,397,644. In both cases, while that cover material is admirably suited for a conventional sanitary napkin, it is seen that the rapid wicking and very dry characteristics typical of those species are quite ill-suited for use as a labial pad. To the contrary, the compositions identified as C and D respond quite differently. Upon initial flow there will be a wicking of fluid into the absorbent core and away from the interface. Over a course of time, that interface will attain a generally steady state flow, passing fluid through the cover at approximately the same rate as it is received. Then, after loading of the absorbent core has begun, and the gradient in moisture is reduced across the cover, even a slight increase in the moisture level (i.e., a decrease in flow gradient) will be seen to occur; although the slight reversal in flow is not a requirement for the cover of the present invention (in this case, it is simply a consequence of adopting specific materials within the most preferred of embodiments as related below). Irrespective of that facet, the covers exhibit the type of physiologically hydrous characteristics deemed most preferred in accordance with the present invention. With the appreciation for the decided advantage provided by a physiologically hydrous cover for pad 30, those skilled in the art will further appreciate the fact that such a characteristic is required principally within the target zone, or that region of the pad disposed within the vestibule. As a matter of manufacturing convenience, this is assured by fabricating the pad with a top cover of appropriate material whereby the entire top surface exhibits this feature. However, that is not an absolute requirement. For example, the physiologically hydrous characteristic may be imparted to the pad by means of coatings or the like applied to the cover (externally or integrally), in which case the same may be confined to the region of the target zone only; i.e., the profile which is intended for interfacial contact with the moist tissue of the vestibule. Other such variations to achieve a zoned distribution of cover properties along these lines will occur to those skilled in the art and, guided by the principles set forth herein, included within the scope of the present invention.

The highly preferred construction outlined above yields a remarkably effective sanitary pad. Fluid is intercepted within the raised profile, and preferably within the target zone identified generally in FIG. 4, after it has been emitted from the vaginal orifice. Prior to a time when this fluid has an opportunity to migrate through the folds of the labia, either forward or rearward as is the case with conventional sanitary napkins, the fluid is caused to contact the profile and be distributed for absorption within the core of the pad. As best viewed in FIG. 9, principal fluid flow is through the physiologically hydrous cover and transfer layer to the oriented microfibrous batts within that region. It is also highly noteworthy to observe a secondary path which is provided during times when increased flow cannot otherwise be accommodated reasonably by the central structure of the pad 30. In this case, fluid may migrate at least in part across the cover (as opposed and/or in addition to through the cover) as shown by the representative arrows in FIG. 9 toward the perimetral sides or edges of the pad. At that juncture, the orientation of the microfibrous batts is again made in the most receptive position relative to flow; whereby that fluid incapable of initial accommodation in the Z direction through the cover and into the absorbent batt is wicked from the edges thereof. Accordingly, a sanitary napkin of materially enhanced absorptive capabilities and collateral reliability in use is provided.

The ability of the labial pad 30 of the present invention to conform anatomically to the wearer's vulva and vestibule area is quite remarkable. Specifically, when disposed initially within the labia majora, the pad 30 of the present invention is self-positioning to a high degree. When the device is properly located by the user, with the prominence 64 disposed in generally abutting engagement with the rearwardmost aspect of the vestibule proximate the anterior labial commissure, a rear line of occlusion is formed thereat. While technically not a true fluid seal, by virtue of the compositional nature of the article, the occluding capabilities as regards the prevention of fluid flow from the rearward area of the vestibule is highly efficient. The normal motion of the user (e.g., walking) tends to reinforce the sealing or occluding effect of the raised region within its zone of engagement with the rearwardmost aspect of the vestibule, thus "sealing" that area. The natural resiliency of the labia tends to compress the body of the pad 30 within the posterior region, with the labia majora lying generally outward of the teardrop-shaped target zone shown in FIG. 4. This slight inward urging or compression provides the line of occlusion within that region. Thus, and as a general consequence of the preferred set imparted to the pad as described above, a highly conforming anatomical fit is achieved which, because that fit relies in part upon the anatomy of the user, is generally self-adjusting. By virtue of the great efficiencies of the oriented microfibrous absorbent webs, providing rapid fluid transfer, that line of sealing or occlusion is generally more than adequate to prevent seepage of fluid outside the zone lying within the vestibule itself. As noted previously, there may be exceptional circumstances during which short duration but heavy flow may not be fully accommodated; however, under these circumstances, the secondary flow path noted with reference to FIG. 9 sufficiently accommodates that eventuality. Regardless of such considerations, the anterior region of the pad 30 lying forwardly of the portion disposed within the vestibule curves gently to conform to the external portion of the vulva of the user as best visualized with reference to FIG. 1. This leaves the clitoris (as well as the other urogenital members) spaced from the pad, unlike many prior art labial constructions, thus guarding against the irritating and perhaps painfully irritating chafing effects which contact can occasion.

The self-conforming characteristics of the labial pad of the present invention render unnecessary a requirement for independent attaching means for the pad. The slight biasing force provided by the wearer's undergarments will establish a sufficient upwardly directed force to maintain the labial pad in the desired position illustrated generally in FIG. 1. However, there may be situations where it is desirable to provide some ancillary attaching means. Accordingly, there is optionally provided a discrete adhesive member identified (in phantom) as 82 in FIG. 3, for securing the pad 30 to the undergarments of a wearer. This adhesive 82 is most preferably a conventional pressure sensitive adhesive bearing a release paper which may be removed to expose the adhesive for purposes of attachment to the undergarment. In this manner, the wearer may exercise the option of attaching the pad or not as a matter of individual preference. It is noteworthy that even in those instances where the option to secure the pad 30 to the undergarment is elected, a comparatively small singular or discrete location or zone for adhesive is most preferably provided as opposed to more conventional longitudinal, multiple strips or the like. Ideally, attachment directly to the undergarment or body is not required, recognizing that such attachment may under some circumstances override the more preferred direct association of the pad solely with the wearer's body; the wearer then facing the possibility that movement of the undergarment relative to the vulva will translate into some motion within the pad itself. Isolating that movement from a single point located near the proximal end of the pad, about which it may pivot, tends to minimize the tendencies toward moving the raised profile of the posterior region of the pad out of its occluding engagement within the vestibule. In this sense, it has been determined that there is a position of relatively neutral action within an undergarment forward of the mons pubis along a type of neutral axis with regard to the legs when the same undergo a walking motion. This neutral point, or so-called point of "stasis," is most preferably the point of cooperative attachment for the adhesive 82. The neutral point is most easily found by considering the pelvic dynamics of a wide range of individuals undergoing walking motion. Such studies reflect the fact that there is a line of neutral motion extending between the legs from a point beginning at about the pubic symphysis and extending directly to the coccyx. This is in most individuals a line of zero motion across what would generally be deemed the median sagittal plane. The optimal point on that plane, for purposes pertinent to the present discussion regarding attachment of the pad 30, is one which is approximately at the pubic symphysis. Accordingly, striving for a point of attachment of the pad by means of a single discrete adhesive spot (or limited multiple spots) at or about the pubic symphysis along the aforementioned line of zero motion is deemed most preferred; although it will normally be found acceptable to have attached the pad at a point lying on or as near as possible to that imaginary line. This approach provides a generally acceptable compromise for those who wish the security of attachment of the pad 30 to the undergarment while that point of attachment is selected as the least influential relative to the potential contribution to rubbing or chafing occasioned by relative motion between the undergarment (and attached pad) and the wearer's vulva.

The labial pad of the present invention is highly commendable for its ease of manufacture both in terms of methodology and selection of materials. As a capsulized summary, the pad 30 utilizes a conventional spunbonded nonwoven bearing a suitable polymeric film as a baffle member corresponding to the bottom surface or face 70. Exemplary of such a baffle is a conventional 0.4 oz. per square yard spunbond web with a 0.75 mil (0.00075 in.) film of an ethylene methyl acrylate, preferably with the EMA side toward the body of the absorbent material. To that baffle member is secured the absorbent body, preferably in the form of two opposed stacks of microfibrous webs 76. Most preferably, the microfibrous webs are surfactant treated polypropylene microfibrous webs having a basis weight of 90 grams per square meter. In order to achieve the optimal orientation wherein the plurality of microfibrous webs are disposed edgewise within the target zone and facewise longitudinally outside that region, two alternate approaches are envisioned. In one instance, two individual stacks of microfibrous webs are disposed in side-by-side relationship along the longitudinal axis "L." Alternatively, a single stack may be disposed upon the baffle member and suitably slitted, at least within the posterior region of the pad and optionally entirely along the length thereof to yield the preferred orientation. When this latter approach is adopted, the fabricator has yet the additional option of slitting some, but not all, of those webs to leave one or more in tact at the interface with the shield or baffle 70. The microfibrous absorbent components are overlaid with a transfer layer 78 preferably comprised of a fibrous blend of polyester, rayon, and a polymeric fiber such as that marketed by C. Itoh & Co. under the tradename "CHISSO". A highly preferred composition is comprised of 60% polyester fibers with a length of approximately ¼" (3 dpf), approximately 20% straight rayon with a fiber length of approximately ⅜" (1.5 dpf) and the balance CHISSO with a fiber length also about ⅜" (3 dpf). Other compositions will occur to those of ordinary skill in the art and may be substituted with due consideration for the functional requirements of a transfer layer in terms of a rather rapid wicking of fluid in the Z direction. That transfer layer also beneficially contributes to a rather "springy" characteristic of the top elements of the pad in order to mold to the wearer's body while providing a soft interface; thus the degree of loft being a salient consideration. Likewise, while principally concerned about efficient Z directional wicking from the cover to the absorbent batt materials, the transfer layer also functions during short duration high flow conditions to distribute fluid in a more transverse direction as need be as may be envisioned with reference to FIG. 9. The transfer layer is overlayed with the preferred physiologically hydrous cover which, as noted above, is selected to maintain a suitably benign physiologically hydrous interface within the environment of the wearer's vestibule. A highly preferred cover is one made from a spunlaced polyester such as that sold under the tradename "SONTARA" by E. I. DuPont Company. Most preferably, a "SONTARA" cover comprised entirely of polyester fiber having a basis weight of about 34 grams per square meter is utilized for this purpose, although suitable equivalents can be adopted provided the same meet the functional requirements aforementioned (e.g., in some instances, even a rayon cover may find good functional utility in this context, as can diverse polymeric materials bearing suitable coatings). The cover is preferably secured to the shield or baffle about the perimetral edges as envisioned best with reference to, e.g., FIGS. 3 and 4, via thermal or adhesive bonding. This yields a border about the perimeter which can vary in width depending upon the fabricator's desires. A pertinent consideration for the border dimension is best considered with reference to the depiction of flow in FIG. 9 which illustrates the alternate flow path provided across the surface of the cover when, e.g., menses may not be accommodated entirely in the Z direction through the cover and into the microfibrous batts. Inasmuch as neither the cover nor the baffle, 80 and 70 respectively, if fluid absorbent under the preferred conditions specified hereinabove, migration of fluid across the cover as shown in FIG. 9 to the perimetral edges will then permit the same to be wicked within the microfibrous batts disposed proximate that juncture. Providing a judiciously sized border will facilitate the ability of fluid to achieve this secondary flow to the absorbent components inasmuch as a border too narrow perhaps will not permit sufficient initial residence time about the edge region for wicking to occur and thereby run off whereas as too wide a border may allow runoff inasmuch as the fluid escapes the region where wicking can occur before that occurrence. A border on the order of about ¼" will under most circumstances be deemed suitable with these thoughts in mind; although, depending upon choice of materials and the like the skilled artisan may need to make specific adjustments which, guided the foregoing principles, are deemed well within the ken of those workers in the field.

As is now quite evident from the foregoing description, the labial pad illustrated in FIGS. 1-10 is highly efficient in use and yet possesses an elegant simplicity of design. That optimization of simplicity and efficiency is carried forward in the packaging of this pad. Several alternatives are illustrated in FIGS. 11-16, to which attention is now directed.

Figure 12:
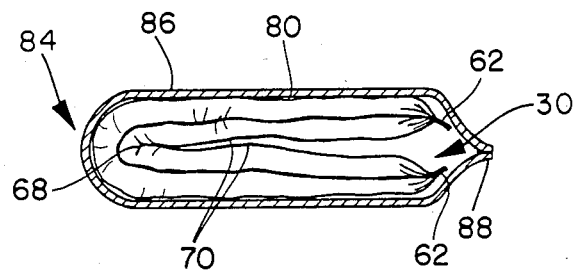
FIG. 12 is a sectional view of the packaging construction shown in FIG. 11 taken substantially along line 12—12 thereof.
Figure 14:
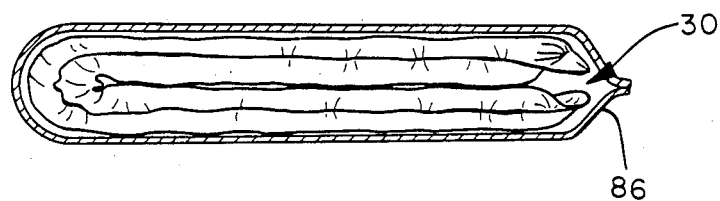
FIG. 14 is a sectional view of the packaging construction of FIG. 13 taken substantially along line 14—14 thereof.
Figure 16:
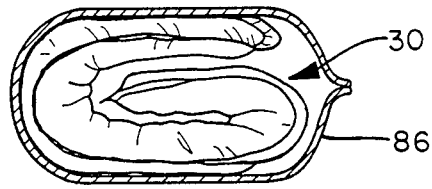
FIG. 16 is a sectional view of the packaging construction illustrated in FIG. 15, taken substantially along line 16—16 thereof.
Figure 11:
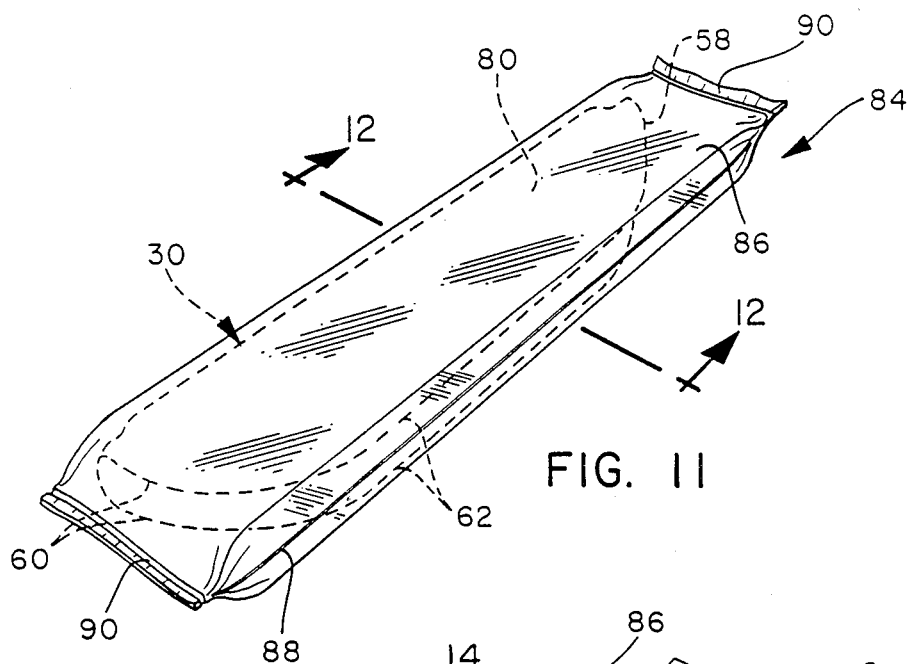
FIG. 11 is an isometric view of a preferred packaging structure for enveloping a labial pad of the present invention, shown partially in phantom lines, disposed therein along a generally longitudinal fold.
Figure 13:
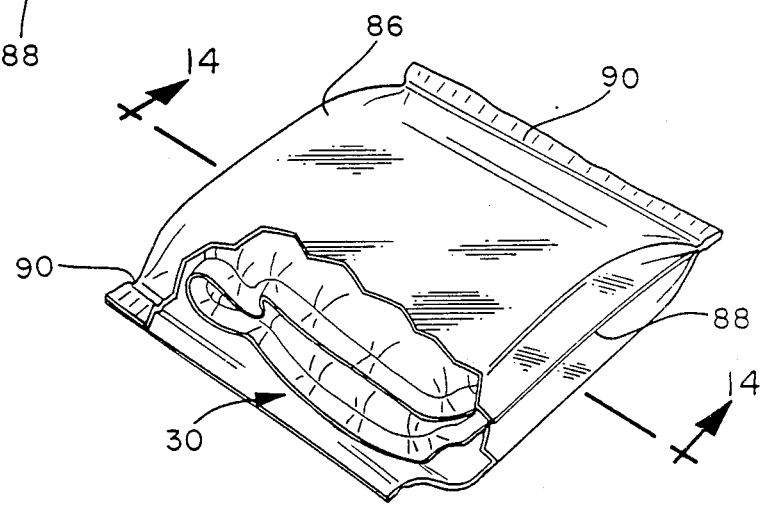
FIG. 13 is an alternate embodiment of a packaging construction for a labial pad in accordance with the present invention, here shown in a perspective view with a portion of the wrapper broken away to reveal the labial pad illustrated in this case to be folded about a generally disposed transverse fold line.
Figure 15:
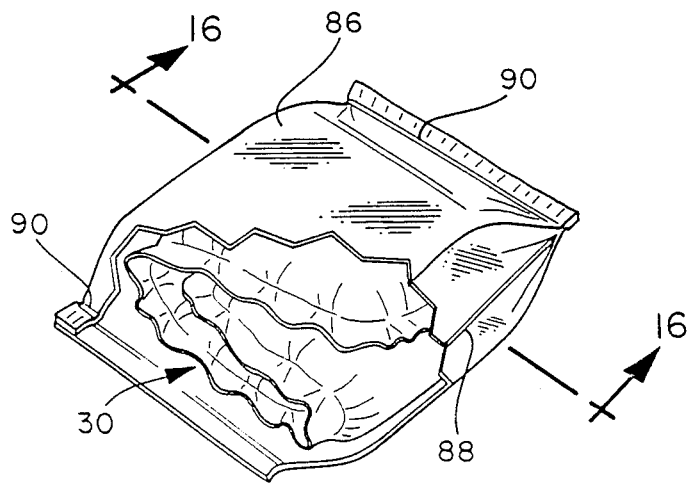
FIG. 15 is an isometric view of still a further alternate embodiment of a packaging construction, similar to that shown in FIGS. 13 and 14, but here depicting the labial pad folded in three generally equal segments about a pair of spaced transverse fold lines.

FIGS. 11 and 12 illustrate a highly preferred packaging configuration for the labial pad of the present invention, designated generally as 84. In this instance the pad 30 is located within a film wrapper 86. The pad is shown folded about the longitudinal axis along the pleat 68; the pad being disposed within the film sheet 86 with the bottom surface 70 folded upon itself across that axis. This preferred embodiment thereby tends to reinforce the set impressed upon the pad during manufacture promoting the proper orientation of components for use. In this particular instance, the packaging wrapper is a thermoplastic film, folded about the pad 30 and sealed along a longitudinal seam 88 and opposed end seams 90. Appropriate selection of materials facilitates normal heat sealing in order to yield a very discreet packaged pad which may be carried conveniently on the person of the wearer in anticipation of use.

Alternate embodiments for wrapped or packaged pads are illustrated in FIGS. 13-16. Inasmuch as the same are conceptually quite similar, only brief explanation will be provided herein. Suffice it to say, in each of these alternate embodiments (recognizing that like parts are continuously identified with like reference characters), the pad 30 is now folded for packaging in a transverse direction as opposed to the longitudinal direction of FIGS. 11 and 12. In the case of the embodiment of FIGS. 13 and 14, the pad is folded once whereas in the case of the embodiment of FIGS. 15 and 16 the pad is folded in thirds.

Just as the present invention envisions alternatives in respect of the method of packaging, there are structural alternatives deemed within the general scope of the present invention which warrant at least brief review. The same are shown in FIGS. 18-21.

FIG. 18 illustrates a more contoured pad (as opposed to, e.g., that of FIG. 2) in accordance with the present invention designated generally as 92. The pad is comprised of a baffle 94 defining a bottom surface and a cover 96 corresponding to that in the previous embodiment; that is, a cover possessing a physiologically hydrous characteristic for proper interface within the vestibule of the wearer. The ovate pad of FIG. 18 includes a raised profile 98 having a prominence 100 within the posterior region of the pad, denoted generally as 102. The profile 98 tapers in this case both rearwardly, toward the distal end 104, and forwardly toward the proximal end 106 at the terminus of the anterior portion of the pad identified as 108. This pad 92, like the pad 30 described in detail above, is configured for partial labial disposition with the raised profile 98 borne interiorly of the labia majora of the wearer, occluding the vestibule over the region defined generally by the posterior labial commissure and the labia majora itself. The raised profile terminates at a point along the longitudinal axis generally corresponding to the departure of the pad element from the vestibule at a location spaced from the clitoris of the wearer. Thus, once again, that highly sensitive genital structure is protected against rubbing contact as has heretofore occurred in many attempts to provide labial interruption in the flow of menses. The pad continues forwardly into external proximate engagement with the wearer's vulva as described relative to the pad 30. Thus, in terms of functionality, the pad 92 is fully comparable to the one described above. And, likewise, the pad 92 with its generally self-conforming anatomical cooperation with the wearer obviates the mandatory requirement for independent attachment means. However, like the embodiment heretofore described, optional garment attachment means (not shown) are included for association at the neutral point of the wearer's undergarment should that be deemed a desirable choice to exercise.

FIG. 19 illustrates another embodiment of a labial pad in accordance with the present invention, denoted generally as 110. The pad 110 is comprised of a baffle 112 of a polymeric film or, optionally, a fibrous web having a polymeric film bonded thereto; in either of such events, the objective being the formation of a fluid impermeable shield. Disposed above that baffle is a first absorbent batt member 114 supporting, in turn, a second absorbent batt 116. In this particular instance, the separate batts 114 and 116 have differing fluid wicking and retaining characteristics, although that is not a mandatory requirement of this embodiment. For example, the upper batt or layer 116 may function more the nature of a transfer layer like the transfer layer 78 provided in the pad 30. Alternatively, the two layers may have differing densities and/or spatial wicking characteristics such that fluid is selectively routed to the outer reaches of the pad should that prove a desirable feature. In other words, the present invention contemplates a plurality of layers comprising the absorbent core, wherein differing layers within such a composite are characterized by differing fluid wicking and/or absorbing properties; such variations being achieved, for example, by incorporating layers of differing chemical and/or physical compositions or properties. Regardless of such considerations, a raised profile in the pad 110 is achieved by means of an insert member identified generally as 118 disposed in mating cooperation with both of the absorbent batts 114 and 116. In the embodiment illustrated, a slot 120 is formed in the upper batt 116, shown in FIG. 19 as a generally rectilinear slot. The insert, comprised of an absorbent, compressed fibrous mass, includes a crown 122 tapering forwardly and rearwardly within the slot 120. The insert 118 further includes a shank 126, lying below the top surface of the batt 116. The bottom face of the shank 126 lies in fluid transmissive engagement with the lower batt 114 in order to transfer, e.g. menses to that component. A cover 128 constitutes the top of the pad structure and is sealed to the baffle 112 about the perimetral edges 130 in a manner similar to that described above relative to the pad 30. The crown of the insert 118 projects sufficiently upward beyond the top surface or plane of the batt 116 to yield a projection or prominence defining a raised profile within the posterior region of the pad. This raised profile is disposed slightly toward the proximal end of the pad in the sense that, as can be envisioned with reference to FIG. 19, the prominence leads to a forward and rearward taper along the longitudinal centerline of the pad. Otherwise, the pad 110 is fully functionally equivalent to the pad 30. That is, the prominence resulting from the insert 118 is provided for partial labial disposition within the vestibule of the wearer to intercept the flow of menstrual fluid. That menstrual fluid first contacts the raised area which defines a target zone within the vestibule, is received within the insert and is then transmitted to both the upper batt 116 and the lower batt 114. Depending upon the wicking characteristics imparted to these member, X-Y-Z directional flow patterns may be tailored by the fabricator as desirable.

FIGS. 20 and 21 depict a further alternate embodiment of a pad in accordance with the present invention, designated generally as 132. This pad is structurally the same as that of FIG. 19, save and except the fact that the insert is now a positionable insert which may be moved by the user of the pad. More specifically, the insert in this instance, designated generally as 134 and best viewed in FIG. 21, is comprised of a base 136 which is formed with a centrally located raised element 138. The upper batt 116, unlike that of the embodiment described with reference to FIG. 19, is a continuous batt member as opposed to the former wherein the slot was formed. In this instance, the insert 134 rides on the base member beneath the cover 128 and may be slid by the user upon an urging motion either forwardly or rearwardly along the longitudinal axis. The insert, when properly positioned to suit the anatomy of the wearer, then functions precisely the same as the insert of FIG. 19. That is, a raised target zone is formed in the nature of a profile configured for disposition within the wearer's vestibule to occlude the same against menstrual flow. The fluid, upon initial contact with the pad 132, is directed through the physiologically hydrous cover member to the insert and then the absorbent batt. Again, while the illustrated embodiment provides plural batts 114 and 116 which may be imparted with different wicking characteristics, those skilled in the art will appreciate that such an option may be foregone in favor of a single absorbent member.

From the foregoing description of alternative constructions available for implementation of the present invention emerges the recognition that a wide range of styles may be adapted to good end in meeting the functional objectives of the present invention. With efficiency and comfort the hallmarks of the labial pad disclosed and claimed herein, structures including a unitary pad or body of proper configuration with zoned fluid distribution and retention characteristics bearing an appropriately physiologically hydrous cover are envisioned. Regardless of the specific structure adopted for implementation, the labial pad of the present invention is remarkable on account of the benefits it provides for the user. Occluding advantages approaching those offered by tampons are imparted to this pad while the safety usually associated with a sanitary napkin is maintained. The pad of the present invention achieves considerably improved fluid distribution and retention, in part by virtue of the microfibrous batts employed in the preferred embodiments, thereby allowing considerable savings in size without sacrifice of efficiency. Comfort is achieved by virtue of the partial (as opposed to total) disposition of the pad within the vestibule combined with the judicious selection of physiologically hydrous cover members. The labial pad of the present invention, regardless of its particular configuration, is highly self-conforming to the anatomy of the wearer, whereby the device moves with that wearer during even vigorous activity as opposed to the more conventional movement of sanitary napkins relative to the body of the wearer. Not only does this minimize the occurrence of chafing or other irritability, it maintains a more positive interrelationship about the zone of occlusion within the vestibule and correlative efficiency of the device. And, the significant improvement experienced in terms of cooperation between pad and wearer is achieved while eliminating the necessity for attachment means or the like leaving the same simply as an option to be exercised by the wearer. Thus, while the invention has now been described with reference to several preferred embodiments and illustrated with regard to a range of optional features, those skilled in the art will appreciate that various substitutions, omissions, modifications, and changes may be made without departing from the spirit hereof. Accordingly, it is intended that the foregoing description be deemed merely exemplary of the preferred scope of the present invention and not to be deemed a limitation thereof.

We claim:

1. A packaged sanitary napkin, said napkin comprising an anatomically, generally self-conforming labial pad configured for disposition within the vestibule of a wearer and for at least partially occluding the same respecting fluid flow therefrom, said napkin comprising a posterior region having a central zone adapted to yield a raised profile for projection within said vestibule and an anterior region merging with said posterior region for generally external disposition about the forward vulvar region of said wearer, said napkin including a top, body-contacting surface divided centrally by a longitudinal axis; wherein said napkin is folded about said longitudinal axis with said top surface lying outwardly, said napkin being disposed within a sealed polymeric packaging film while in a folded configuration.

2. A packaged sanitary napkin, said napkin comprising an anatomically, generally self-conforming labial pad configured for disposition within the vestibule of a wearer and for at least partially occluding the same respecting fluid flow therefrom, said napkin comprising a posterior region having a central zone adapted to yield a raised profile for projection within said vestibule and an anterior region merging with said posterior region for generally external disposition about the forward vulvar region of said wearer, said napkin including a top, body-contacting surface bisected by a transverse axis; wherein said napkin is folded parallel to said transverse axis, said napkin being disposed within a sealed polymeric packaging film while in a folded configuration.

* * * * *